United States Patent [19]

Muth et al.

[11] Patent Number: 5,322,925
[45] Date of Patent: Jun. 21, 1994

[54] ABSORBABLE BLOCK COPOLYMERS AND SURGICAL ARTICLES MADE THEREFROM

[75] Inventors: Ross R. Muth, Brookfield; Nagabhushanam Totakura; Cheng-Kung Liu, both of Norwalk, all of Conn.

[73] Assignee: United States Surgical Corporation, Norwalk, Conn.

[21] Appl. No.: 33,897

[22] Filed: Mar. 19, 1993

Related U.S. Application Data

[63] Continuation-in-part of Ser. No. 969,420, Oct. 30, 1992, abandoned.

[51] Int. Cl.$^5$ .................. C08G 63/08; C08G 63/00; A61M 11/00
[52] U.S. Cl. .................. 528/354; 525/408; 525/415; 528/357; 528/361; 606/230; 606/231
[58] Field of Search .................. 525/415, 408; 528/354, 528/357, 361; 606/230, 231

[56] References Cited

U.S. PATENT DOCUMENTS

| | | | |
|---|---|---|---|
| 4,243,775 | 1/1981 | Rosensaft et al. | 525/415 |
| 4,300,565 | 11/1981 | Rosensaft et al. | 525/415 |
| 4,429,080 | 1/1984 | Casey et al. | 528/354 |
| 4,705,820 | 11/1987 | Wang et al. | 524/381 |
| 4,788,979 | 12/1988 | Jarrett et al. | 528/354 |
| 4,857,602 | 8/1989 | Casey et al. | 528/428 |
| 4,863,472 | 9/1989 | Törmälä et al. | 603/16 |
| 4,882,168 | 11/1989 | Casey et al. | 404/468 |
| 4,891,263 | 1/1990 | Kotliar et al. | 428/225 |
| 4,916,193 | 4/1990 | Tang et al. | 525/413 |
| 4,916,207 | 4/1990 | Boyle, Jr. et al. | 528/370 |
| 4,920,203 | 4/1990 | Tang et al. | 525/409 |
| 4,942,875 | 7/1990 | Hlavacek et al. | 606/230 |
| 4,968,317 | 11/1990 | Törmälä et al. | 606/77 |
| 4,997,440 | 3/1991 | Dumican | 528/354 |
| 5,037,950 | 8/1991 | Bezwada et al. | 528/354 |
| 5,066,772 | 11/1991 | Tang et al. | 528/354 |
| 5,080,665 | 1/1992 | Jarrett et al. | 606/219 |
| 5,120,802 | 6/1992 | Mares et al. | 525/415 |
| 5,145,945 | 9/1992 | Tang et al. | 528/370 |
| 5,152,781 | 10/1992 | Tang et al. | 528/354 |
| 5,185,408 | 2/1993 | Tang et al. | 525/415 |
| 5,252,701 | 10/1993 | Jarrett et al. | 528/354 |

FOREIGN PATENT DOCUMENTS 1604178 12/1981 United Kingdom .

OTHER PUBLICATIONS

M. S. Roby et al., "Absorbable Sutures Based on Glycolide/Trimethylene Carbonate Copolymers".

*Primary Examiner*—John Kight, III
*Assistant Examiner*—Shelley A. Dodson

[57] ABSTRACT

Block copolymers have a first copolymer block wherein lactide is the predominant component and a second copolymer block wherein trimethylene carbonate is the predominant component. The copolymers are useful in forming surgical devices, including monofilament sutures.

25 Claims, 2 Drawing Sheets

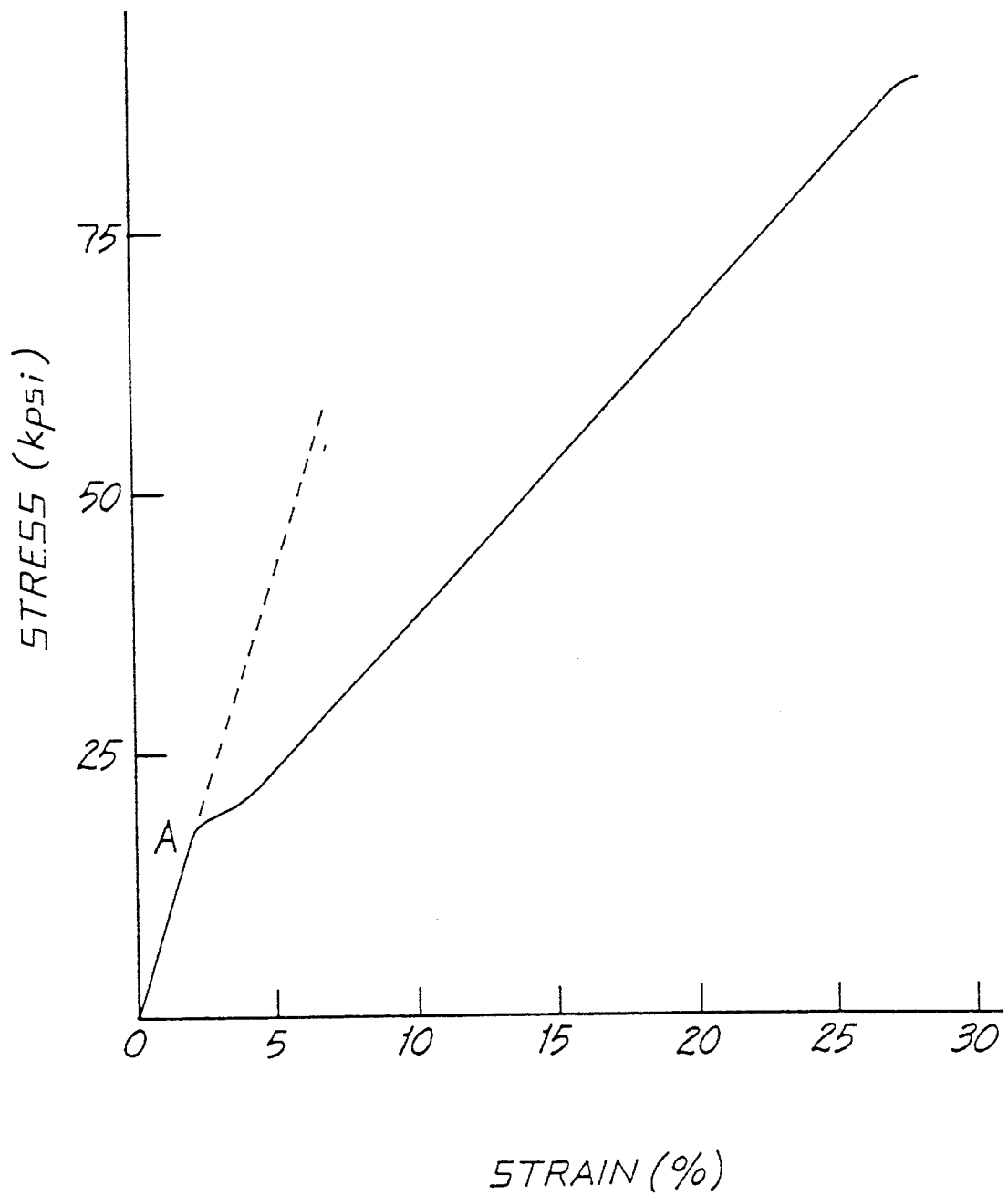

ized at 150°-220° C, under vacuum, for periods of time rang-
ABSORBABLE BLOCK COPOLYMERS AND SURGICAL ARTICLES MADE THEREFROM

CROSS REFERENCE TO RELATED APPLICATION

This application is a continuation-in-part of copending U.S. application Ser. No. 07/969,420, filed Oct. 30, 1992 abandoned.

FIELD OF THE INVENTION

The present invention relates to absorbable block copolymers having a block which is predominantly lactide and a block which is predominantly trimethylene carbonate. This invention also relates to surgical articles made from such copolymers.

BACKGROUND OF THE INVENTION

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D.K. Gilding et al., "Biodegradable polymers for use in surgery-polyglycolic/poly (lactic acid) homo-and copolymers: 1, "*Polymer*, Volume 20, pages 1459-1464 (1979), and D. F. Williams (ed.), *Biocompatibility of Clinical Implant Materials*, Volume II, chapter 9: "Biodegradable Polymers" (1981).

Surgical devices prepared from copolymers containing lactide or glycolide and trimethylene carbonate have been described, for example, in U.S. Pat. No. 4,429,080 which describes glycolide-trimethylene carbonate random copolymers and triblock copolymers having glycolide end blocks and glycolide-trimethylene carbonate random copolymer middle blocks. As another example, U.S. Pat. No. 5,066,772 describes random copolymers of lactide and trimethylene carbonate and triblock copolymers having lactide end blocks and lactide-trimethylene carbonate random copolymer eater blocks. In addition, see U.S. Pat. Nos. 4,243,775; 4,300,565; 4,705,820; 4,891,263; 4,916,193; and 4,920,203.

SUMMARY OF THE INVENTION

It has now been found that absorbable surgical articles may be formed from a block copolymer comprising a first block formed from a copolymer having lactide as the predominant component thereof and a second block formed from a copolymer having trimethylene carbonate as the predominant component thereof. A "predominant component" is a component which is present in an amount greater than fifty mole percent.

In particularly useful embodiments, the absorbable block copolymers of the present invention can be spun into fibers. These fibers are useful as monofilament sutures, can be braided to form multifilament sutures, or can be incorporated into absorbable or partially absorbable surgical elements.

The copolymers of this invention have desirable physical characteristics such as longer absorption times compared to glycolide/lactide copolymers and greater strength retention in vivo than the glycolide-glycolide/trimethylene carbonate-glycolide triblock copolymer of the prior art.

BRIEF DESCRIPTION OF THE DRAWINGS

FIG. 3 illustrates the stress-strain behavior of a monofilament fiber prepared in accordance with the present invention.

DETAILED DESCRIPTION OF THE INVENTION

Figure 1A:
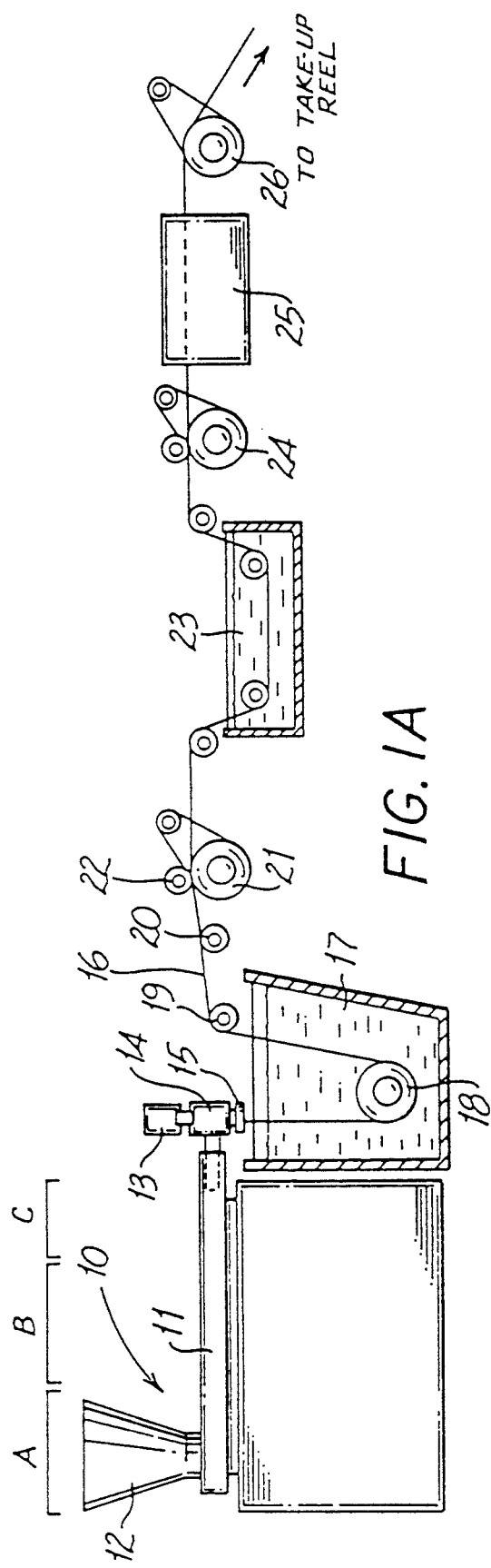
FIGS. 1A and 1B are a schematic illustration of an extrusion and stretching operation useful in producing sutures in accordance with this invention.

In accordance with the present invention, it has been found that two specific types of copolymers, one having lactide as the predominant component thereof and one having trimethylene carbonate as the predominant component thereof, can advantageously be combined to form a block copolymer useful in forming surgical elements.

The block copolymer compositions of the present invention include a first block formed from a copolymer which has lactide as the predominant component thereof. That is, lactide comprises at least 50 mole percent of the first block. Preferably, lactide comprises at least about 70 mole percent of the first block. Most preferably, the first block is about 80 mole percent of lactide. The lactide may be copolymerized with any monomer which provides an absorbable copolymer to form the first block. Such monomers include but are not limited to glycolide, p-dioxanone and $\epsilon$-caprolactone, with glycolide being preferred. The glycolide/lactide copolymers useful in the practice of the present invention have a molecular weight such that their inherent viscosity is from about 0.9 to about 2.5 dl/g preferably from about 1.0 to about 1.8 dl/g measured at 30° C. at a concentration of 0.25 g/dl in chloroform or hexafluoroisopranol (HFIP). The copolymers of lactide which form the first block can be random or block copolymers and can be synthesized by known methods. See, for example, U.S. Pat. No. 3,636,956 the disclosure of which is incorporated herein by reference.

The second block of the compositions of this invention are formed from a copolymer having trimethylene carbonate as the predominant component. That is, trimethylene carbonate comprises at least 50 mole percent of the second block. Preferably, trimethylene carbonate comprises at least about 70 mole percent of the second block. Most preferably, the second block comprises about 80 mole percent of trimethylene carbonate. The trimethylene carbonate may be copolymerized with any monomer which provides an absorbable copolymer to form the second block. Such monomers include but are not limited to glycolide, lactide, p-dioxanone and $\epsilon$-caprolactone, with glycolide being preferred. For purposes of the present invention, trimethylene carbonate copolymers having an inherent viscosity of from about 0.75 to about 1.5 dl/g measured at 30° C. and a concentration of 0.25 g/dl in chloroform of HFIP may generally be used. The copolymers of trimethylene carbonate which form the second block can be random or block copolymers and can be synthesized by known methods. See, for example, U.S. Pat. Nos. 5,066,772, 4,916,193 and 4,891,263 the disclosures of which are incorporated herein by reference.

In forming the block copolymers of this invention, the first, predominantly lactide block may be present in an amount from about 10 to about 90 percent by weight based on the weight of the final block copolymer. The second, predominantly trimethylene carbonate block may be present in an amount from about 10 to about 90 weight percent based on the weight of the final block copolymer. Preferably, the second block comprises between about 15 and about 50 weight percent of the block copolymer. In a particularly useful embodiment, the first block comprises about 70 weight percent and the second block comprises about 30 weight percent of the final block copolymer.

The block copolymers of this invention may be formed into surgical articles using any known technique, such as, for example, extrusion, molding and/or solvent casting. The copolymers may be used alone, blended with other absorbable compositions, or in combination with non-absorbable components. Preferably, however, the copolymers are spun into fibers to be used as sutures, either monofilament or multifilament, or are woven with other fibers, either absorbable or nonabsorbable, to form meshes or fabrics. The spinning and braiding of copolymer fibers to form multifilament sutures can be accomplished by any known technique such as those described, for example, in U.S. Pat. Nos. 5,019,093 and 5,059,213, the disclosures of which are incorporated herein by reference.

A wide variety of surgical articles can be manufactured from the copolymers of the present invention. These include but are not limited to sutures, staples, clips and other fasteners, wound dressings, drug delivery devices, pins, screws and other implants.

Figure 2:
FIG. 2 is a depiction of a needled suture in accordance with the present invention.

Surgical articles made from the polymers of this invention can be used to secure tissue in a desired position. A suture in accordance with the present invention, suture 101, may be attached to a surgical needle 100 as shown in FIG. 2 by methods well known in the art. Wounds may be sutured by approximating tissue and passing the needle suture through tissue to create would closure. The needle preferably is then removed from the suture and the suture tied.

As previously mentioned, the surgical elements of the present invention exhibit longer absorption times compared to glycolide/lactide copolymers and greater in vivo strength retention compared to the glycolide-glycolide/trimethylene carbonateglycolide ABA triblock copolymers of the prior art.

The following examples are illustrative of the copolymers of the present invention and surgical elements made therefrom.

EXAMPLE 1

Preparation of the First Block

A copolymer of glycolide and lactide is prepared as follows:

Hydroxyacetic acid (glycolic acid) is heated under nitrogen to 180° C. to remove impurities such as water. Pressure is then reduced and heating is continued for two hours to yield a prepolymer of polyglycolic acid, which is recovered and powdered.

The prepolymer is heated in the presence of $Sb_2O_3$ at 275° C. under low pressure with an argon purge and stirring. The prepolymer cracks and glycolide is distilled over and recovered in a cold vacuum receiver. Preferably, the glycolide is purified by conventional techniques, such as distillation, crystallization, and sublimation.

L-lactide is used alone or in combination with a small amount of the DL racemer. L-lactide is purified by crystallization from toluene solution. The DL racemer, if used, is purified by crystallization from ethyl acetate.

A mixture of the purified glycolide (20 mole percent) and lactide (80 mole percent) is charged to a reactor under an argon blanket. A solution of stannous octoate catalyst in diethyl ether is added to give 0.02% w. of catalyst, based on the total weight of glycolide and lactide. The reactor is further purged with argon and held at 5 psi while heating to 170°–175° C. Pressure and temperature are maintained for six hours.

The reaction product is isolated, comminuted, and treated to remove residual reactants. Any method capable of removing the unreacted monomers from the crude reaction product may be used. A preferred purification procedure is as follows.

After comminution, the crude reaction product is contacted with ethyl ether for about 72 hours in a Soxhlet-type extractor to remove unreacted monomer. Typically, 4–10% of the starting monomers remain unreacted, and the glass transition temperature of the crude copolymer is approximately 50° C. Removal of unreacted monomers raises the glass transition temperature. As will be understood by one skilled in the art, the composition of the copolymer may differ slightly from the composition of the starting monomeric mixture because the lactide and glycolide are not of equal reactivity.

After the extraction period, the partially purified copolymer is slowly heated under vacuum from ambient temperature to 140° C. over a period of about 48 hours. The slow rate of heating is desirable to prevent melting (strictly speaking, flowing together) of the copolymer particles and to remove any water present. Desirably, dry inert gas is used to purge the system, and occasionally the heating step may require more than 48 hours to reach the desired glass transition temperature. The combination of slow heating and purging with dry gas removes any residual solvent (ethyl ether) present, thereby raising the glass transition temperature.

After removal of unreacted monomers (and of solvent, if solvent extraction is used), the purified copolymer is further dried if it was not dried enough in the monomer removal step and, in any event, stored to keep it dry.

EXAMPLE 2

Preparation of the Block Copolymer

Trimethylene carbonate (1168 grams; 11.45 /moles) is added to a reactor and dried at 24°±2° C. for 16 hours. Then 332 grams (2.86 moles) of glycolide which had been dried for 16.5 hours at 24°±2° C. is added to the reactor along with 1.0 gram of stannous octoate. The mixture in the reactor is heated at 150° C. for 3.5 hours in a nitrogen atmosphere to polymerize the glycolide/trimethylene carbonate copolymer.

The copolymer of Example 1 (3500 grams) is then added to the reactor, and polymerization is continued for an additional 28 hours at 160° C.

EXAMPLE 3

The procedure of Example 2 is followed, except that rather than add the preformed glycolide-lactide copolymer, glycolide and lactide monomer are added to the reactor. Specifically, glycolide (586 grams; 5.05 moles) and lactide (2913.2 grams; 20.21 moles) which had been previously vacuum dried at 24°±2° C. for 20 hours are then added to the reactor. Polymerization is continued at 160° C. for another 28 hours.

The resulting product containing 70 percent by weight of random glycolide-lactide copolymer blocks and 30 percent by weight of random glycolide-trimethylene carbonate blocks. The glycolide-lactide blocks contain 80 mole percent lactide, and the glycolide-trimethylene carbonate blocks contain 80 mole percent trimethylene carbonate.

EXAMPLE 4

Glycolide (553.4 grams; 4.77 moles) and trimethylene carbonate (1946.6 grams; 19.1 moles) and 1.0 gram stannous octoate are dried in a reactor overnight at 24°±2° C. under vacuum. The contents are heated to 150° C. until molten, and then polymerization is carried out for 24 hours with stirring. Then 419.1 grams (3.6 moles) of glycolide and 2080.9 grams (14.4 moles) L-lactide which is previously dried are added to the reactor, and polymerization is allowed to continue at 160° C. with stirring for another 24 hours. The polymer is extruded and post-treated to remove unreacted monomers. The resulting copolymer contains 50 percent by weight of blocks of a glycolide/trimethylene carbonate random copolymer having 20 mole percent glycolide and 80 mole percent trimethylene carbonate and 50 percent by weight of blocks of a glycolide/lactide random copolymer having 20 mole percent glycolide and 80 mole percent lactide.

EXAMPLE 5

Glycolide (2214 grams; 19.1 moles) is dried in a reactor at 24°±2° C. overnight. Then, 778.6 grams (7.63 moles) of trimethylene carbonate and 1.0 gram stannous octoate both of which are previously dried overnight at 24°±2° C. under vacuum, are added to the reactor. The temperature within the reactor is brought to 150° C. with stirring and polymerization is allowed to proceed for 2 hours. Then, 1026.7 grams (8.85 moles) of glycolide and 2973.3 grams (20.63 moles) of lactide which are previously dried for 24 hours at 24°±2° C., are added to the reactor and polymerization is allowed to continue at 150° C. for another 20 hours and 15 minutes. The temperature of the polymerization is raised to 190° C. for 2 hours and 45 minutes and then the polymer is extruded. The extruded polymer is post-treated to remove the unreacted monomers using those methods known to the art. One of such methods is described above in connection with Example 1.

The resulting copolymer contains 20% by weight of blocks of a random copolymer of glycolide and trimethylene carbonate having 20 mole percent glycolide and 80 mole percent trimethylene carbonate, and 80% by weight of blocks of a random glycolide/lactide copolymer having 30 mole percent glycolide and 70 mole percent lactide.

EXAMPLE 6

Glycolide (166.03 grams; 1.43 moles), 584.00 grams (5.73 moles) of trimethylene carbonate, 3.21 grams of diethylene glycol and 1.0 gram stannous octoate are dried overnight at 24° C. under vacuum in a reactor. The temperature within the reactor is brought to 160° C. with stirring and polymerization is allowed to proceed for 10 hours and 30 minutes. Once polymerization is complete, 348.83 grams (3 moles) of glycolide and 3901.15 grams (27.07 moles) of lactide which are previously dried for 24 hours at 24°±2° C., are added to the reactor with no stirring and the temperature within the reactor is raised to 170° C. Stirring is restarted and polymerization is allowed to continue at 170° C. for another 19 hours.

The resulting copolymer contains 15% by weight of blocks of a random copolymer of glycolide and trimethylene carbonate having 20 mole percent glycolide and 80 mole percent trimethylene carbonate, and 85% by weight of blocks of a random glycolide/lactide copolymer having 10 mole percent glycolide and 90 mole percent lactide.

EXAMPLE 7

Lactide (260.08 grams; 1.809 moles), 739.2 grams (7.25 moles) of trimethylene carbonate, 3.21 grams of diethylene glycol and 1.0 gram stannous octoate are dried in a reactor overnight at 24°±2° C. under vacuum. The temperature within the reactor is brought to 160° C. and polymerization is allowed to proceed with stirring for 7 hours. Once polymerization is complete, 670.6 grams (5.78 moles) of glycolide and 3329.4 grams (23.1 moles) of lactide which are previously dried for 24 hours at 24°±2° C., are added to the reactor with no stirring and the temperature within the reactor is raised to 170° C. Stirring is restarted and polymerization is allowed to continue at 170° C. for another 22¾ hours. The polymer is extruded and post-treated to remove unreacted monomers.

The resulting copolymer contains 20% by weight of blocks of a random copolymer of lactide and trimethylene carbonate having 20 mole percent lactide and 80 mole percent trimethylene carbonate, and 80% by weight of blocks of a random glycolide/lactide copolymer having 20 mole percent glycolide and 80 mole percent lactide.

EXAMPLE 8

Glycolide (125.72 grams; 1.084 moles) is added to a reactor and dried at 24°±2° C. for 16 hours. Then, 624.88 grams (4.335 moles) of dried lactide is added to the reactor along with 1.0 grams of stannous octoate. The mixture in the reactor is heated at 160° C. for 3.5 hours in a nitrogen atmosphere to polymerize the glycolide/lactide copolymer.

Lactide (576.6 grams; 4.00 moles) and trimethylene carbonate (3673.4 grams; 36.01 moles) is dried at 24°±2° C. for 20 hours and then is added to the reactor. Polymerization is continued at 160° C. for another 28 hours.

The resulting polymer containing 15% by weight blocks of 20:80 glycolide/lactide random copolymer and 85% by weight blocks of 10:90 lactide/trimethylene carbonate random copolymer.

The block copolymers of the present invention can be extruded into monofilament sutures using any known extrusion technique.

EXAMPLE 9

Lactide (942 grams; 6.54 moles), 1558 grams (15.27 moles) of trimethylene carbonate, 5 grams of glycolic acid and 1.2 gram stannous octoate are dried in a reactor overnight at 24±2° C. under vacuum. The temperature within the reactor is brought to 160° C. and polymerization is allowed to proceed with stirring for 6 hours. Once polymerization is complete, 1128 grams (9.72 moles) of glycolide, 6374 grams (44.22 moles) of lactide, and 3.5 grams of stannous octoate which are previously dried for 24 hours at 24°±2° C., are added to the reactor with no stirring and the temperature within the reactor is raised to 170° C. Stirring is restarted and polymerization is allowed to continue at 170° C. for another 6 hours. The polymer is extruded and post-treated to remove unreacted monomers.

The resulting copolymer contains 25% by weight of blocks of a random copolymer of lactide and trimethylene carbonate having 30 mole percent lactide and 70 mole percent trimethylene carbonate, and 75% by weight of blocks of a random glycolide/lactide copolymer having 18 mole percent glycolide and 82 mole percent lactide.

Figure 1B:
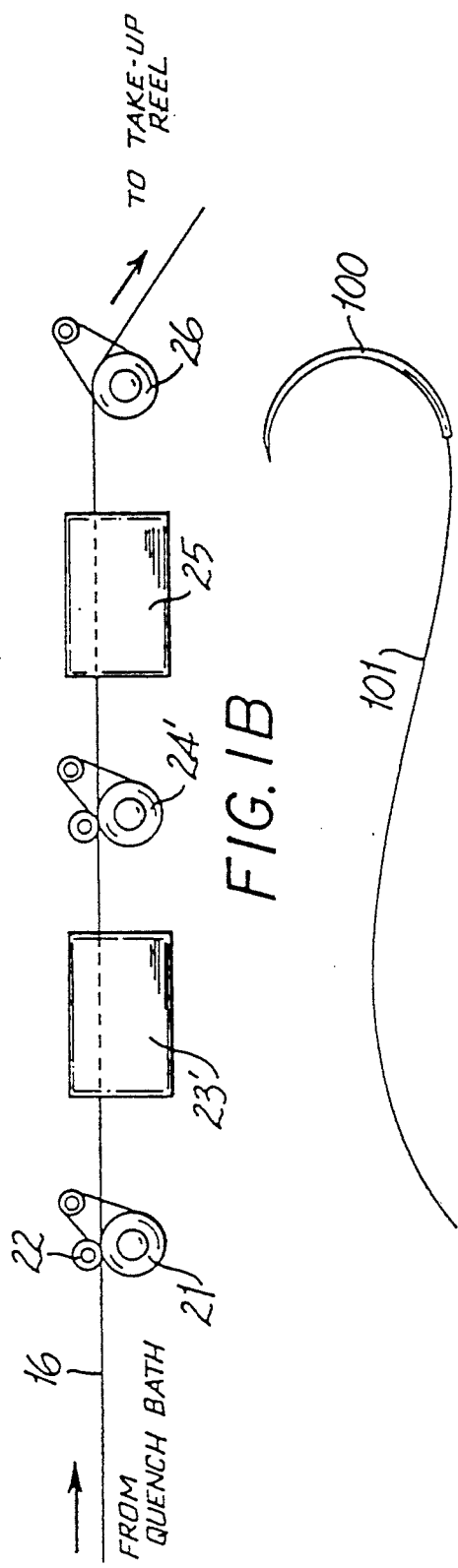

FIGS. 1A and 1B schematically illustrate preferred extrusion and stretching operations for producing monofilaments of the copolymers of this invention. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of the block copolymer are introduced to the extruder through drier-hopper 12.

Motor-driven metering pump 13 delivers extruded copolymer at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling of the monofilament in some unpredictable manner. In general, barrel zone A of the extruder can be maintained at a temperature of from about 100° to 180° C., zone B at from about 120° to 200° C. and zone C at from about 130° to about 210° C. Additional temperature parameters include: metering pump block 13 at from about 130° to about 210° C., spin pack 14 at from about 130° to about 210° C., spinneret 15 at from about 140° to about 220° C. and quench bath 17 at from about 20° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sizes 4/0 to 8/0, monofilament 16 is drawn through heating unit 23, which can be an oven chamber or a hot water trough, by means of second godet 24 which rotates at a higher speed than first godet 21 thereby stretching the monofilament from three to nine times its original length. Where heating unit 23 is an oven chamber, its temperature is advantageously maintained at from about 40° to about 140° C. and preferably from about 60° to about 120° C. In the case of larger sutures, e.g., sizes 2 to 3/0, it is preferred that heating unit 23 be a hot liquid trough or bath which is maintained at a temperature of from about 40° to about 98° C. and preferably from about 60° to about 90° C.

For smaller suture sizes, e.g., sizes 6/0 to 8/0, it is preferred to pass the monofilament through a second heating unit, e.g., maintained at a temperature of from about 40° to about 140° C. and preferably from about 50° to about 120° C., by means of a hot air oven to heat-treat the monofilament prior to the equilibration and annealing operations. This second heat treatment results in on-line relaxation, or shrinkage, of the monofilament, e.g., for a recovery of from about 85 to about 97 percent, and preferably from about 90 to about 95 percent, of the stretched length of the monofilament. In order to accommodate this on-line shrinkage in the monofilament, the third godet is driven at a speed which is somewhat less than that of the second godet.

Following stretching and orientation (and, optionally, the aforedescribed second heat treating step for smaller sutures sizes), monofilament 16 from godet 24 is taken up on a spool which is then set aside for a period of time sufficient to permit the monofilament to achieve a condition of equilibrium as previously defined. While the period of equilibration may vary depending on the particular copolymer composition employed and/or the conditions under which the copolymer is extruded, cooled and oriented, in most cases storage of the monofilament following its orientation for at least about 6 hours, preferably at least about 3 days and more preferably at least about 24 hours. It is generally preferred that the spooled monofilament be stored at ambient temperature, e.g., 18°–23° C., and a dew point below −12° C.

In the larger suture sizes, e.g., sizes 5/0 and larger, annealing is accomplished by shrinkage of the suture, e.g., for a recovery of from about 75 to about 95 percent, and preferably from about 80 to about 90 percent, of its stretched length.

In carrying out the annealing operation, the desired length of equilibrated suture may be wound around a creel and the creel placed in a heating cabinet circulated with nitrogen and maintained at the desired temperature, e.g., 70° C. After a suitable period of residency in the heating cabinet, e.g., about 20 minutes to 24 hours, the suture will have undergone shrinkage, e.g., to about 85% of the stretched length for sutures of sizes 2 to 3/0, to about 90% of the stretched length for sutures of sizes 4/0 and 5/0 and essentially no shrinkage in the case of sutures of sizes 6/0 to 8/0. The creel may be rotated within the heating cabinet in order to insure uniform heating of the monofilament or the cabinet may be of the circulating hot air type in which case uniform heating of the monofilament will be achieved without the need to rotated the creel. Thereafter, the creel with its annealed suture is removed from the heating cabinet and when returned to room temperature, the suture is removed from the creel, conveniently by cutting the wound monofilament at opposite ends of the creel.

The sutures, optionally attached to surgical needles, are then ready to be packaged and sterilized.

EXAMPLE 10

Monofilament sutures manufactured in accordance with the above-described process using the copolymer of Example 3 were tested for straight pull strength, Young's modulus and in vitro strength retention. Straight pull strength was tested in accordance with the test procedure described in ASTM D-2256. An Instron Tester Model No. 4301 (Instron Corporation, Canton, Mass.) was used to determine straight pull strength. Knot pull tensile strength was tested in accordance with U.S.P. XXI, tensile strength sutures (881). Young's modulus, which is a measurement of flexibility, is the initial modulus as determined from the slope of stress-strain curves produced in the straight-pull strength tests. Young's modulus is the ratio of applied stress to strain in the elastic region (initial linear portion of curves, AO) as illustrated in FIG. 2. The in vitro strength retention of the suture was tested as follows:

To simulate in vivo conditions, the suture samples were stored in a container filled with Sorenson's buffer solution at 37° C. After various period of time, the suture samples were then removed from the container to test their knot-pull strength, using a Instron tensile tester. In vitro knot-pull strength retention is indicative of in vivo strength retention.

The results of the tests are presented in Table I. In the strength retention data reported in Table I, $T_n$ represents the time elapsed in weeks since the sample was placed in the solution, with n representing the number of weeks. For comparison purposes, the same tests were conducted on a Maxon suture, which is made from a glycolide/glycolide-trimethylene carbonate/glycolide copolymer (commercially available from Davis & Geck, Danbury, CT).

TABLE I

| Suture | Straight Pull Strength (kpsi) | Knot Pull Strength (kpsi) | Young's Modulus (Kpsi) | In Vitro Strength Retention (% Strength Remaining) | | | | | | |
|---|---|---|---|---|---|---|---|---|---|---|
| | | | | $T_1$ | $T_2$ | $T_3$ | $T_4$ | $T_6$ | $T_8$ | $T_{10}$ |
| Example 10 | 59 | 39 | 400 | 89 | 89 | 82 | 67 | 34 | 12 | — |
| MAXON | 78–88 | 41–70 | 435–495 | — | 66 | — | 17 | 0 | 0 | 0 |

As the data in Table I demonstrates, the suture made of a copolymer of the present invention showed superior in vitro strength retention while demonstrating acceptable straight and knot pull strengths and Young's modulus.

What is claimed is:

1. A block copolymer comprising:
   a) a first block formed from a copolymer having lactide as the predominant component therefore copolymerized with one or more comonomers selected from the group consisting of glycolide, p-dioxanone and ε-caprolactone; and
   b) a second block formed from a copolymer having trimethylene carbonate as the predominant component thereof copolymerized with one or more comonomers selected from the group consisting of glycolide, lactide, p-dioxanone and ε-caprolactone.

2. A copolymer as in claim 1 wherein said first block comprises lactide in an amount greater than about 70 mole percent.

3. A copolymer as in claim 1 wherein said first block comprises about 80 mole percent lactide.

4. A copolymer as in claim 1 wherein said second block comprises trimethylene carbonate in an amount greater than about 70 mole percent.

5. A copolymer as in claim 1 wherein said second block comprises about 80 percent trimethylene carbonate.

6. A copolymer as in claim 1 wherein said first block comprises from about 10 to about 90 percent by weight of the block copolymer.

7. A copolymer as in claim 1 wherein said second block comprises from about 10 to about 90 percent by weight of the coplymer.

8. A copolymer as in claim 1 wherein said first block comprises about 70 percent by weight of the block copolymer and said second block comprises about 30 percent by weight of the block copolymer.

9. A copolymer as in claim 1 wherein said first block comprises about 75% by weight of the block copolymer and contains about 80 percent lactide, the remainder of said first block being glycolide, and said second block comprises about 25% by weight of the block copolymer, and contains about 70 percent trimethylene carbonate, the remainder of said second block being lactide.

10. A surgical article comprising one or more fibers made from a block copolymer having a first block comprising a copolymer having lactide as the predominant component thereof copolymerized with one or more comonomers selected from the group consisting of glycolide, p-dioxonane and ε-caprolactone and a second block comprising a copolymer having trimethylene carbonate as the predominant component thereof copolymerized with one or more comonomers selected from the group consisting of glycolide, lactide, p-dioxanone and ε-caprolactone.

11. A surgical article as in claim 10 wherein said first block comprises lactide in an amount greater than about 70 mole percent.

12. A surgical article as in claim 10 wherein said first block comprises about 80 mole percent lactide.

13. A surgical article as in claim 10 wherein said second block comprises trimethylene carbonate in an amount greater than about 70 mole percent.

14. A surgical article as in claim 10 wherein said second block comprises about 80 percent trimethylene carbonate.

15. A surgical article as in claim 10 wherein said first block comprises from about 10 to about 90 percent by weight of the block copolymer.

16. A surgical article as in claim 10 wherein said second block comprises from about 10 to about 90 percent by weight of the copolymer.

17. A surgical article as in claim 10 wherein said first block comprises about 70 percent by weight of the block copolymer and said second block comprises about 30 percent by weight of the block copolymer.

18. A surgical article as in claim 10 wherein said first block comprises about 75% by weight of the block copolymer and contains about 80 percent lactide, the remainder of said first block being glycolide, and said second block comprises about 25% by weight of the block copolymer and contains about 70 percent trimethylene carbonate, the remainder of said second block being lactide.

19. A surgical article as in claim 10 wherein said surgical element is a suture.

20. A surgical article as in claim 10 wherein said surgical article is selected from the group consisting of staples, clips and other fasteners, would dressings, drug delivery devices, pins, screws and other implants.

21. A surgical article as in claim 20 wherein said surgical article is a bone pin.

22. An absorbable surgical suture comprising a block copolymer having a first block formed from a copolymer having lactide as the predominant component thereof copolymerized with one or more comonomers selected from the group consisting of glycolide, p-dioxonane and $\epsilon$-caprolactone and a second block formed from a copolymer having trimethylene carbonate as the predominant component thereof copolymerized with one or more comonomers selected from the group consisting of glycolide, lactide, p-dioxanone and $\epsilon$-caprolactone.

23. An absorbable suture as in claim 22 wherein said suture retains at least about 30 percent of its in vitro strength after 6 weeks.

24. An absorbable suture as in claim 22 wherein said first block comprises about 75% by weight of the block copolymer and contains about 80 percent lactide, the remainder of said first block being glycolide, and said second block comprises about 25% by weight of the block copolymer and contains about 70 percent trimethylene carbonate, the remainder of said second block being lactide.

25. A method of closing a wound comprising suturing with a suture made at least in part from the copolymer of claim 1.

* * * * *